United States Patent [19]
Whisson

[11] Patent Number: 5,762,632
[45] Date of Patent: Jun. 9, 1998

[54] INFUSION SET

[75] Inventor: Maxwell Edmund Whisson, Perth, Australia

[73] Assignee: Eastland Technology Australia Pty Ltd, West Perth, Australia

[21] Appl. No.: 617,772

[22] PCT Filed: Sep. 23, 1994

[86] PCT No.: PCT/AU94/00579

§ 371 Date: Mar. 19, 1996

§ 102(e) Date: Mar. 19, 1996

[87] PCT Pub. No.: WO95/09019

PCT Pub. Date: Apr. 6, 1995

[30] Foreign Application Priority Data

Sep. 27, 1993 [AU] Australia ............... PM1468

[51] Int. Cl.$^6$ ................................. A61M 5/00
[52] U.S. Cl. ........................... 604/171; 604/174
[58] Field of Search ................... 604/171, 174, 604/175, 177, 192, 198, 162, 263, 272

[56] References Cited

U.S. PATENT DOCUMENTS

| | | | |
|---|---|---|---|
| 4,676,783 | 6/1987 | Jagger et al. | 604/171 |
| 5,067,946 | 11/1991 | Zhadanov | 604/192 X |
| 5,108,376 | 4/1992 | Bonaldo | 604/177 X |
| 5,152,749 | 10/1992 | Giesy et al. | 604/272 X |
| 5,192,275 | 3/1993 | Burns | 604/263 |
| 5,380,293 | 1/1995 | Grant | 604/177 |
| 5,395,347 | 3/1995 | Blecher et al. | 604/192 X |

FOREIGN PATENT DOCUMENTS

B-14896/92 10/1993 Australia.
A-54775/94 8/1994 Australia.
2109608 10/1971 Germany.

OTHER PUBLICATIONS

Copy of International Publication No. WO 88/07387 dated 6 Oct. 1988 entitled "Retractable Safety Needle".
Copy of International Publication No. WO 92/08502 dated 29 May 1992 entitled "Catheter Assembly Having Safety Means".
Copy of International Publication No. WO 94/11050 dated 16 May 1994 entitled "Catheter Introducer Assembly Including Needle Shield".

*Primary Examiner*—Sam Rimell
*Assistant Examiner*—Luke Yeh
*Attorney, Agent, or Firm*—Merchant, Gould, Smith, Edell, Welter, & Schmidt, P.A.

[57] ABSTRACT

A infusion set which comprises a base (11) which is adapted to be capable of being manipulated by a user to effect insertion or removal of the infusion set and supporting a hollow needle (12) where the hollow needle has a pointed free end (18) and the other end of the hollow needle is supported from the base, a flexible delivery tube having one end connected to the other end of the needle and a portion at a position spaced from its one end being supported from a housing (14) and where a flexible duct (23) is concentrically provided over the flexible tubing (13) between the base (11). The flexible tubing being capable of slidable movement within the duct to cause slidable movement of the needle (12) in the base (11). The housing (14) has an engagement means (27) movable on the housing (14) and in engagement with the flexible tubing (13) to cause the slidable movement of the needle (12) in the base (11) between an extended position and a retracted position on movement of the engagement means.

22 Claims, 7 Drawing Sheets

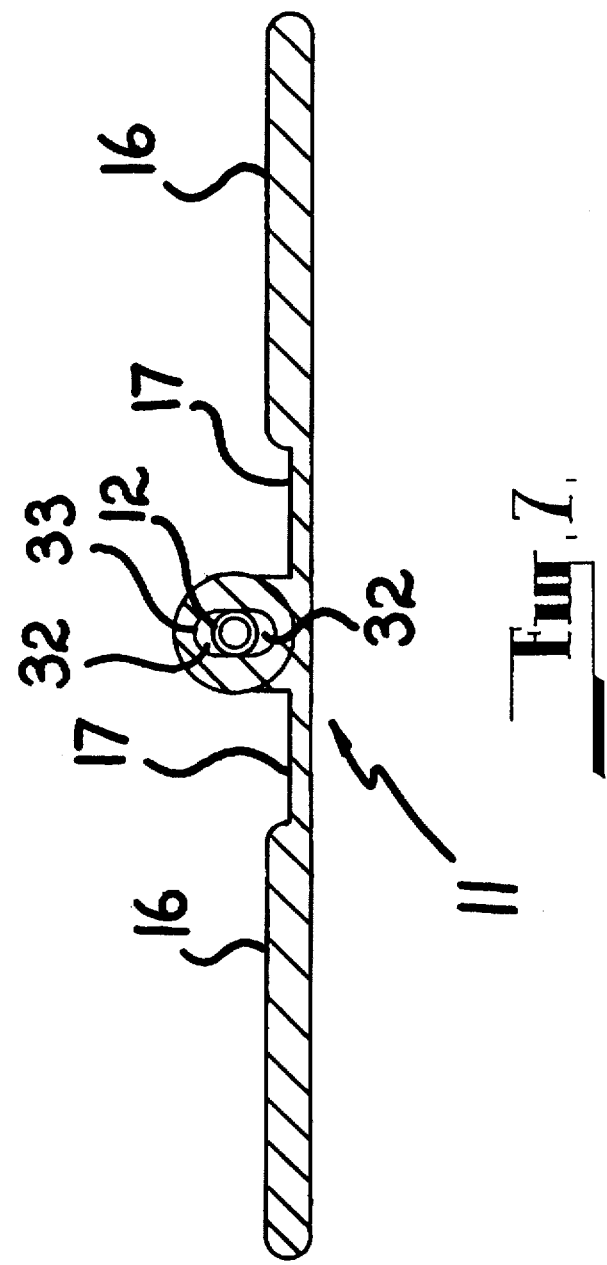

INFUSION SET

THIS INVENTION relates to an infusion set.

Throughout the specification she term "infusion set" shall be taken as comprising a base adapted to be capable of being manipulated by a user to effect insertion or removal of the infusion set, a hollow needle having one pointed free end and the other end supported from the base and a flexible delivery tube connected at one end to the other end of the needle, the other end of the flexible delivery tube being adapted to be connected to a receptacle or delivery means.

Infusion sets of the type described above are associated with a very high incidence of accidental needle stick injury. One reason for such is because in use, after the user has removed the line from the vein of a patient the needle is usually held such that it is suspended from the flexible delivery tubing and is therefore able to move in a unpredictable manner due to the flexible resilient nature of the flexible delivery tubing. Also the needle can be difficult to control when suspended from the flexible delivery tubing when being carried to a safe "sharps" disposal container and then can be difficult to insert in to the "sharps" container without the risk of puncturing the hands or arms of the user. There is also significant danger to any persons in the vicinity of the user when the used infusion set is being carried. Furthermore, such infusion sets carry a high risk of transmission of infection such as HIV, Hepatitis and the like ailments due to the substantial quantity of blood remaining within the infusion set.

It is an object of this invention to provide an infusion set which on completion of its use can be rendered safe.

In one form the invention resides in an infusion set where a portion of the flexible delivery tube is supported at a position spaced from its one end from a housing and where a flexible duct is concentrically provided over the flexible tubing between the base and the housing to enable slidable movement of the flexible tubing within the duct, said needle being longitudinally slidable in the base, said housing having an engagement means movable on the housing and in engagement with the flexible tubing to cause longitudinal movement of the needle in the base between an extended position and retracted position on movement of the engagement means.

According to a preferred feature of the invention, a delivery tube is substantially inextendable.

According to a further preferred feature of the invention, the needle is substantially incapable of rotation about its central axis with respect of the base. This can be achieved in one embodiment by forming the portion of the needle accommodated within the base when in the extended position to be asymmetric about its central axis and a passage formed in the base of a complementary cross-sectional configuration. One form of asymmetry comprises forming the needle to be convoluted. Alternatively, the needle may be supported within the base by a hub which is slidably received in the base and if desired the hub may be configured such that it is incapable of rotation within the passage. This latter function can be achieved by forming the hub to be non circular and the passage of complementary configuration.

According to a preferred feature of the invention, the needle when in the retracted position is engaged with the base to prevent movement from the retracted position to the extended position. In addition, the needle is preferably engagable with the base when at the extended position to prevent movement from the extended position until after a predetermined force has been applied to the needle by the delivery tube. The retention of the needle in the extended position and the retracted position may be provided by a first detent means and a second detent means respectively in the base which is engagable by the needle and/or the hub supporting the needle when at the extended or retracted position respectively.

According to a further preferred feature of the invention, the engagement means is incapable of a movement with respect to the housing which would enable longitudinal movement of the needle from the retracted position to the extended position. In addition, the accommodation of the delivery tube within the housing is such as to prevent movement of the delivery tube from the housing into the flexible duct. In addition, the engagement means may take the form of a slider slidably supported on the housing or alternatively a capstan-like element rotatably supported on the housing.

The invention will be more fully understood in the light of the following description of one specific embodiment. The description is made with reference to the accompanying drawings of which;

FIG. 7 is a sectional end elevation of the base and needle according to the embodiment.

Figure 1:
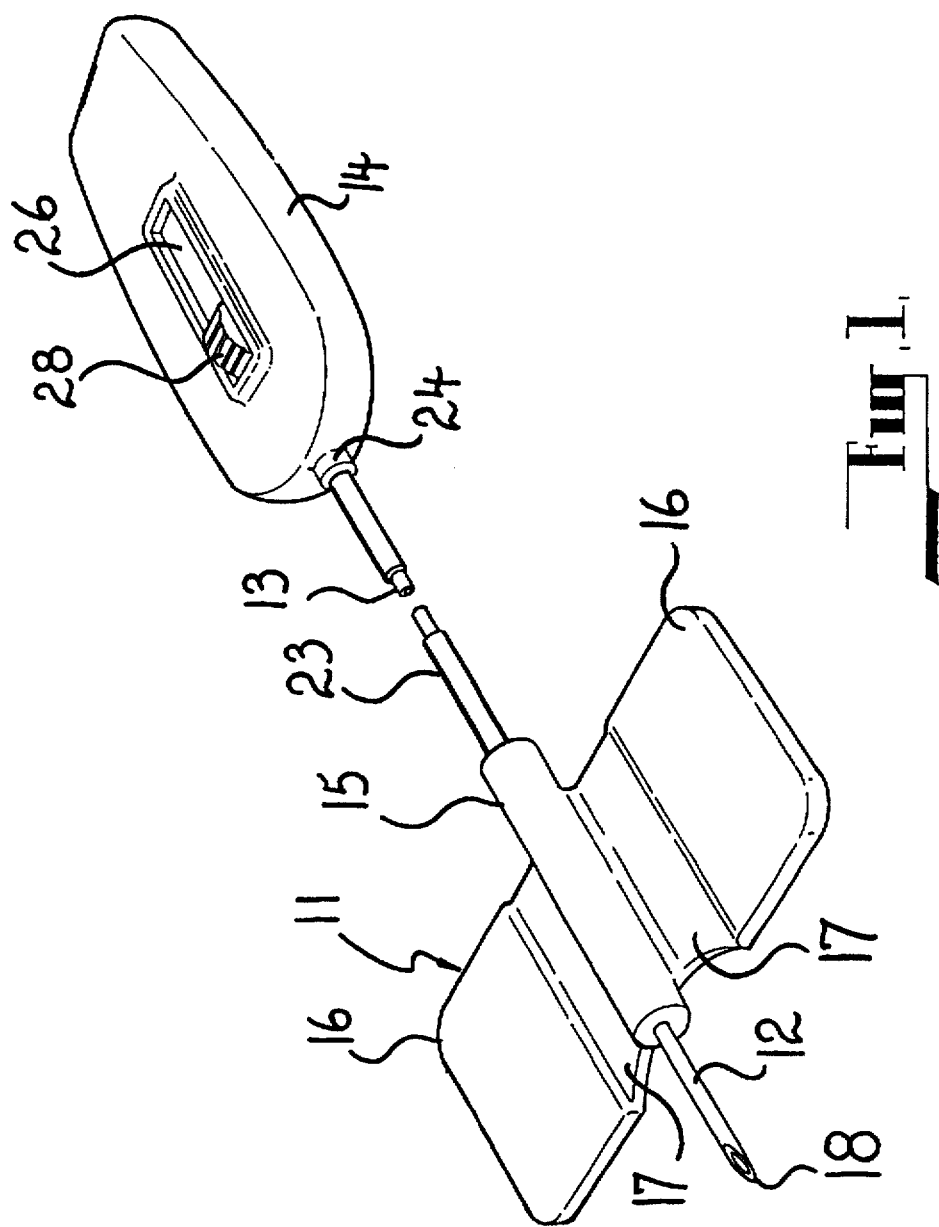
FIG. 1 is an isometric view of an infusion set according to the embodiment.
Figure 2:
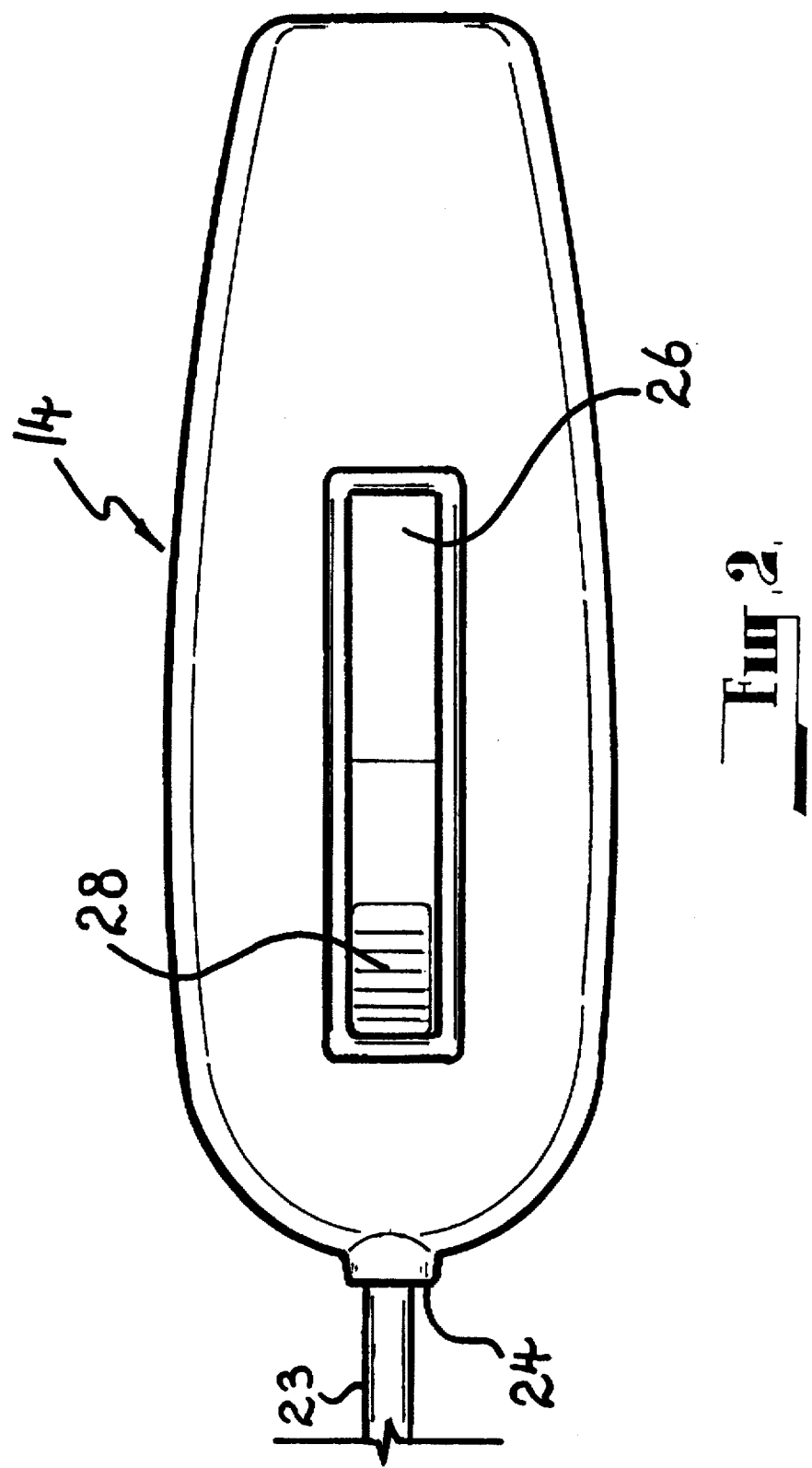
FIG. 2 is an upper plan view of the housing of the embodiment.
Figure 3:
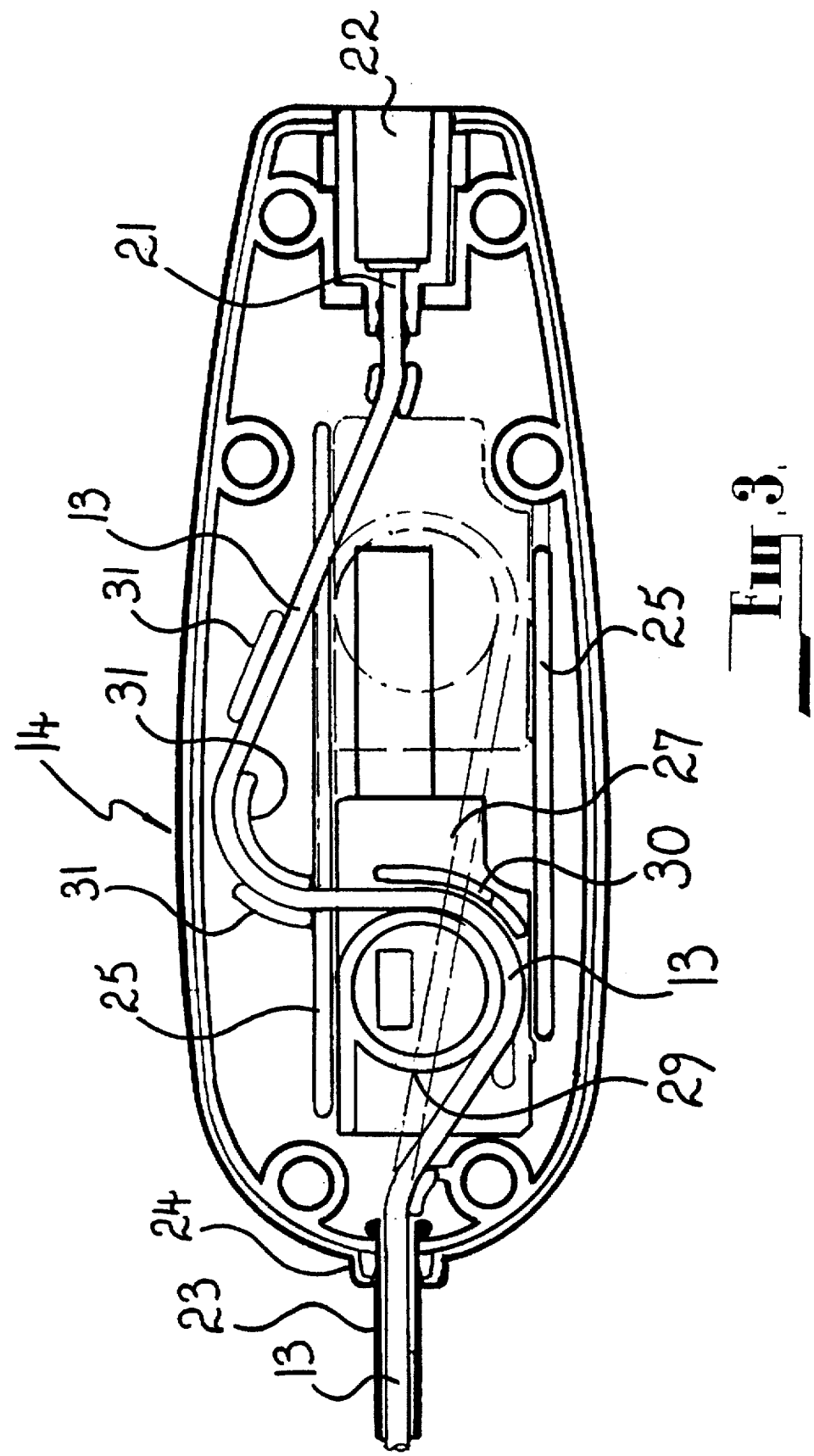
FIG. 3 is a sectional plan view of the housing according to the embodiment.
Figure 4:
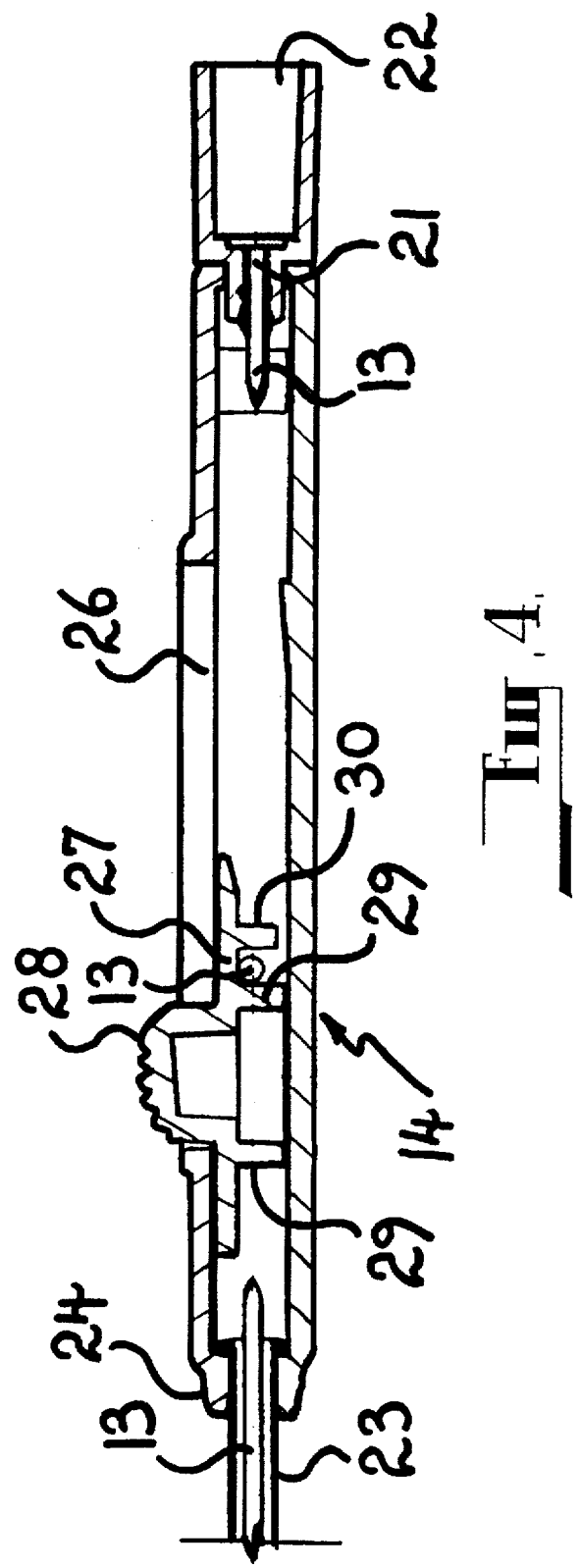
FIG. 4 is a sectional side elevation of the housing according to the embodiment.
Figure 5:
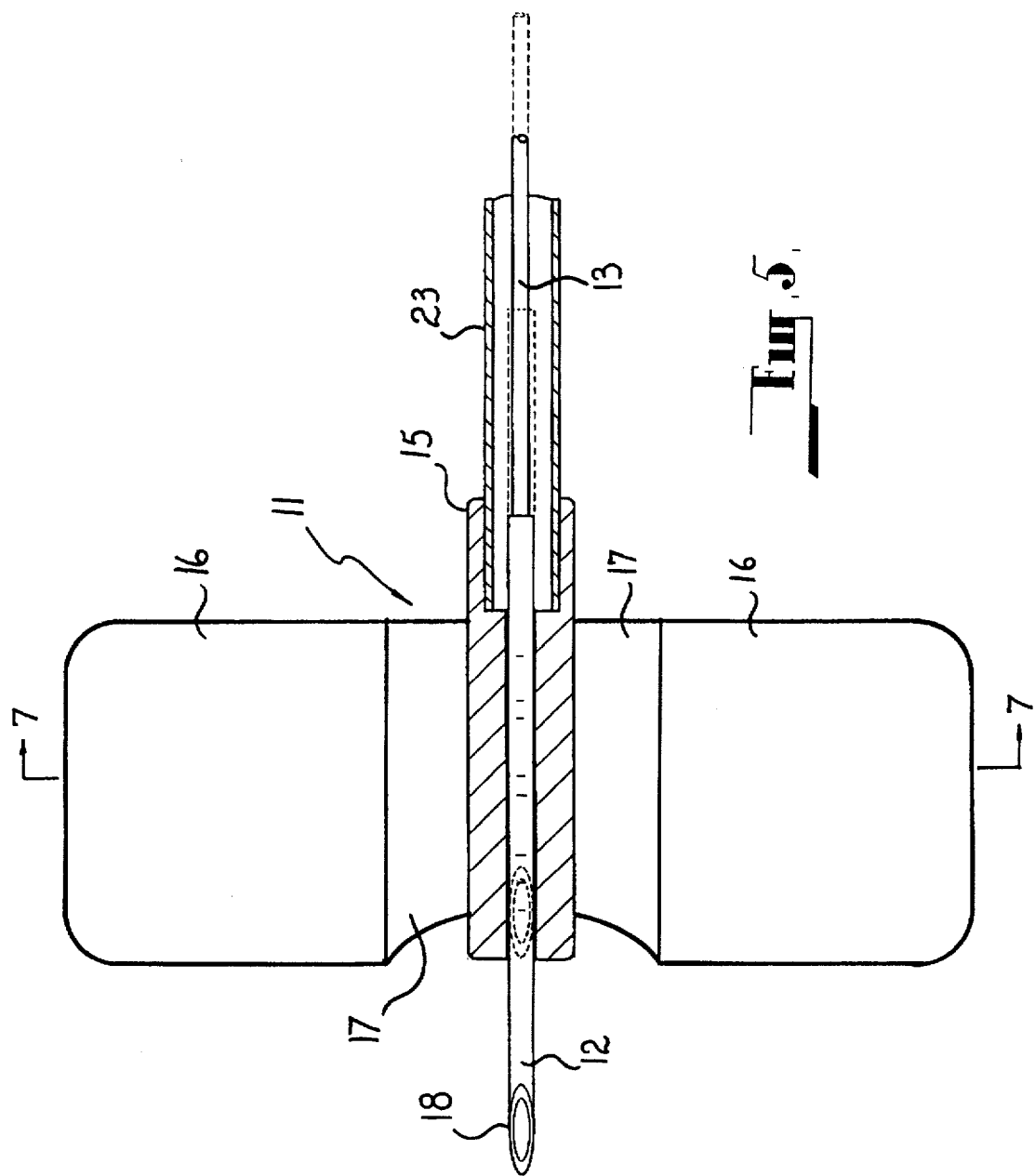
FIG. 5 is a sectional plan view of the base and needle according to the embodiment.

The infusion set according to the embodiment comprises a base 11, a needle 12, a flexible delivery tube 13 received within a flexible duct 23 and a housing 14.

The base 11 comprises a central tubular member 15 with a pair of lateral wing members 16 mounted thereto in diametrically opposed relation. The junction between the wing members 16 and the tubular portion 15 are provided with a reduced thickness portion to provide a hinged connection 17 between the wings 16 and the tubular portion 15. In use, the wings 16 occupy the position as shown at which they extend to opposite sides of the tubular portion 15. When in that position they can be fixed to the arm or body of patient by use of suitable tape. When it becomes necessary to insert the infusion set, the wings 16 are hinged to a position (not shown) at which they are substantially adjacent and parallel to each other whereby they can be grasped between a thumb and a finger of the user to enable insertion.

Figure 6:
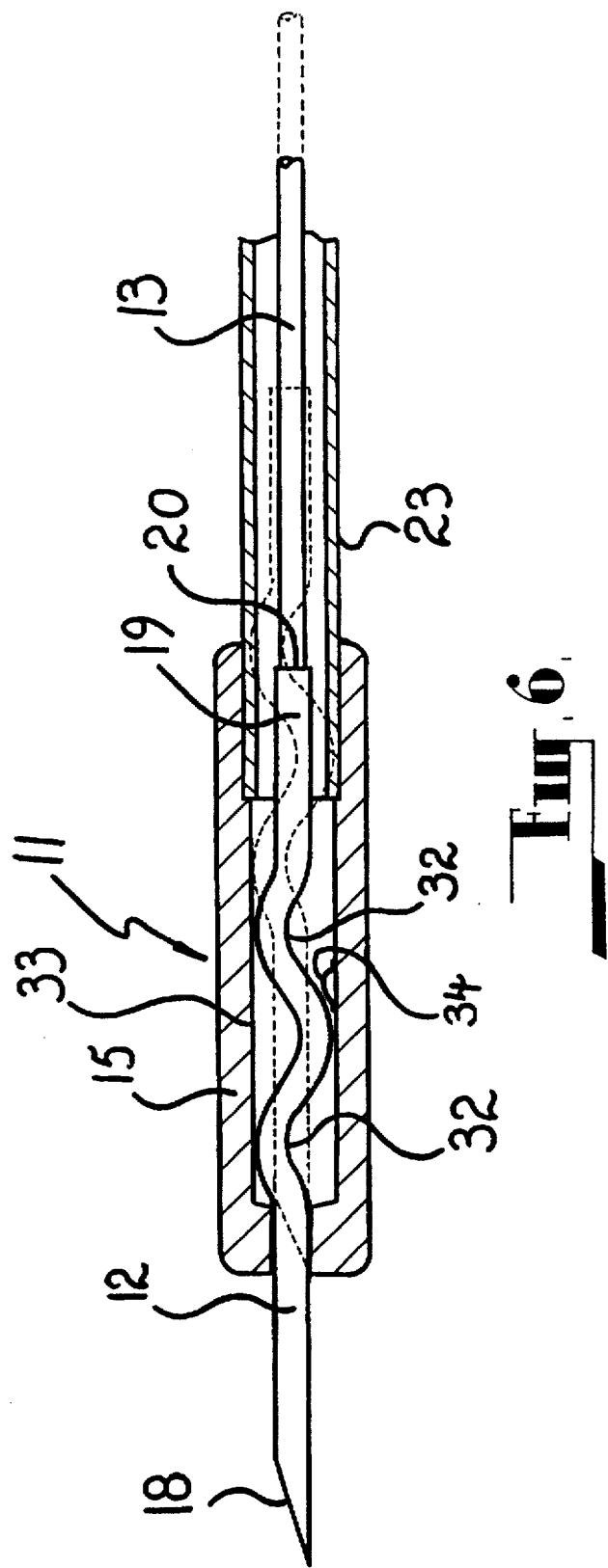
FIG. 6 is a sectional side elevation of the base and needle according to the embodiment.

The needle 12 is hollow and has one end 18 which is free and formed to a sharp point, while the other end 19 (see FIG. 6) is connected to one end 20 of the flexible delivery tube 13, whereby the interior of the hollow needle 12 is in open communication with the interior of the flexible delivery tube 13. The needle 12 is slidably supported within the tubular member 15. The flexible delivery tube 13 is received within the body of the housing 14 such that it enters the interior of the housing 14 at the proximate end of the housing 14 most adjacent the base 11 and is fixed at its other end 21 to the remote end of the housing 14 which is most remote from the base 11. The flexible delivery tube is substantially inextensible. This may be effected by choice of the appropriate material or associating it with a fine wire bonded or fixed to the tube and fixed at one end to the tubular portion 13 and at the other end to the housing 14.

The remote end of the housing 14 is provided with a socket 22 which is shaped to sealingly receive the "LUER" fitting of a conventional syringe or receptacle used in relation to such infusion set and the other end 21 of the flexible delivery tube is fixed to the socket 22. Alternatively, the socket may be configured to sealingly receive any other conventional fitting which may be able to be used. Such a fitting may comprise a port or similar plug which can be pierced by a syringe or like means to sealingly deliver an agent to the delivery tube 13.

The base 15 is supported from the proximate end of the housing 14 by a flexible tubular duct 23 which is concentrically received over the flexible delivery tube 13 and is fixed at one end to the base 15 and at the other end to a tubular boss 24 provided at the proximate end of the housing. The flexible tubular duct 23 may take any suitable form and need not be sealed. If desired it may incorporate or comprise a closely wound wire coil.

The interior of the housing 14 is provided with a pair of parallel guides 25 spaced to each side of the central axis between the proximate and remote end of the housing 14 and the wall of the upper face of the housing is formed with a longitudinal slot 26 which is located intermediate of the ribs 25. The ribs support between themselves the engagement means which takes the form of a slider 27 which is slidably received between the ribs 25 for longitudinal movement within the housing 14 and which is associated with a control knob or handle 28 which is received within the slot 26 whereby the knob may be manipulated to cause slidable movement of the slider 27 within the housing 14.

The slider 27 is provided with a circular boss 29 which is associated with a concentric part circular arcuate rib 30 at the side of the boss remote from the proximate end of the housing 14 to define channel shaped space between the boss 29 and the arcuate rib 30 which is able to slidably receive the flexible delivery tube 13.

The housing is further provided with a set of guide ribs 31 adjacent one exterior face of one of the longitudinal ribs 25. The guide ribs serve to define a convoluted pathway which is an extension of that defined between the boss 29 and the arcuate rib 30 on the slider 27.

The portion of the flexible delivery tube 13 which is accommodated within the housing 14 is received in the convoluted pathway defined between the boss 29 and arcuate rib 30 on the slider 27 and the guide ribs 31 provided in the housing. The pathway is such that when the slider 27 is at its first position adjacent the proximate end of the housing 14 the pathway defined for the flexible tubing is arcuate whereby no kinks are induced in the flexible delivery tubing 13.

The engagement between the slider 27 and the flexible tubing 13 is such that on the slider 27 being moved longitudinally within the housing away from the proximate end thereof to its second position adjacent the remote end, a portion of flexible delivery tubing 13 accommodated within the duct 23 is drawn into the interior of the housing 14 which consequently causes the movement of the needle 12 into the tubular portion 15 of the base 11. When the slider is at its second position most adjacent the remote end of the housing 14 the flexible delivery tube 13 has been sufficiently drawn into the body of the housing 14 to enable full retraction of the needle 12 into the tubular portion 15 and such that the free end 18 of the needle is unexposed. The flexible nature of the flexile delivery tube 13 is such that on the slider 27 being moved from its second position most adjacent the remote end of the housing 14 to its first position most adjacent the proximate end of the housing 14 the portion of the flexible tubing within the housing 14 is not caused to re-enter the delivery duct 23 but will be caused to flex.

The mounting of the needle 12 within the tubular portion 15 is such that the needle is incapable of relative rotational movement within the tubular portion 15. In the case of the embodiment this is effected by forming the inner portion of the needle 12 with a series of convolutions which are substantially coplanar. The passageway in the tubular portion 15 is formed at its end adjacent the housing with an expanded portion of oval cross section which is shaped to be able to receive the convoluted portion of the needle 12. The interengagement of the convolutions 32 within the expanded portion 33 of the passageway within the tubular portion 15 serves to prevent relative rotation of the needle 12 with respect to the base 11. Furthermore, on retraction of the needle 12 into the tubular portion 15 of the base 11 as a result of the flexible delivery tube 13 being drawn into the housing 14, the convolutions are drawn into the duct 23 and become frictionally engaged with the inner wall of the duct 23. Such frictional engagement serves to resist any tendency that the flexible delivery tube may have to re-enter the duct 23 from the housing 14 on movement of the slider 27 from its second position to its first position.

In order to retain the needle 12 in the extended position a detent such as a dimple 34 in the interior of the expanded portion 33 of the passageway in the tubular portion 15, engages a convolution when the needle 12 is in the extended position. The dimple 34 provides sufficient resistance for the needle to be inserted into the body of a patient but such resistance can be overcome by the retractable movement of the slider 27.

If desired the slider 27 may be associated with a locking means which will ensure locking engagement between the slider 27 and the body of the housing 14 on the slider 27 being moved to its retracted position. Furthermore, the housing 14 may be associated with suitable stops or detent means (not shown) which will provide a tactile indication to the user on movement of the control knob 28 to indicate that the knob has been moved to either of its end positions.

In another embodiment the base may be formed such that on manipulation of the wings 16 the passage accommodating the needle is changed in cross-sectional configuration whereby when the wings are in their natural unstressed state the needle is held in position and when the wings are folded in a particular manner the needle is able to move in the passage. In such an arrangement the needle is also retained in position when the wings have been folded to a position enabling the base to be held by an operator by the folded wings and the needle inserted into the body of the patient.

The means for retracting the needle need not have the form as described in relation to the embodiment but may comprise any means of causing retraction of the flexible delivery tube into the body of the housing 14 to effect retraction of the needle 12.

In an alternative embodiment the engagement means may comprise a capstan or a like element which is rotatably supported on or in the housing and which is able to wind the flexible delivery tube into the housing. If desired, the capstan is only rotatable on the housing in one direction in order to enable a retractable movement of the needle only.

In addition, in both embodiments the movement of the engaging means to the retracted position may cause a destructive bending or "kinking" of the delivery tube to render the infusion set incapable of further use. In the case of the embodiment described above in relation to the drawings the arrangement of the slider with respect to the base is such that in the event of inadvertent movement of the slider from the retracted position to the extended position the delivery tube folds up or "kinks" rather than causing movement of the needle to the extended position.

Furthermore the configuration applied to the needle to ensure that it is not capable of rotation within the base may taken any desirable form.

In a further embodiment the needle is unconvoluted and is provided with a hub member which is slidably received in the tubular member. The hub is associated with a first detent to retain the needle in the extended position during use from which it can be released with appropriate force being applied to the delivery tube. The hub may be associated with a second detent or similar engagement means which engages and retains the hub and needle in the retracted position.

In another embodiment the first detent may comprise a protrusion in the passage towards the outer end which is positioned and shaped to be engaged by the free end of the needle when the needle is moved to the retracted position. The arrangement is such that on the needle being moved to the retracted position the free end moves past the protrusion and if an attempt is made to move the needle to the extended position the free end engages the protrusion to prevent further movement of the needle out of the passage.

It should be appreciated that the scope of the invention should not be limited to the particular scope of the above embodiment.

THE CLAIMS defining the invention are as follows;
I claim:

1. An infusion set comprising:
   a portion of a flexible delivery tube which is supported at a position spaced from one end of the tube from a housing;
   a flexible duct which is concentrically provided over the flexible delivery tube between a base and the housing to enable slidable movement of the flexible delivery tube within the duct; and
   needle being received in the one end of the flexible delivery tube, the needle further being longitudinally slidable in the base, said housing having an engagement means movable on the housing for engaging the flexible delivery tube to cause longitudinal movement of the needle in the base between an extended position and a retracted position on movement of the engagement means.

2. An infusion set as claimed in claim 1 wherein the delivery tube is not extendible.

3. An infusion set as claimed in claim 1 wherein the needle is not rotatable about a central axis of the needle with respect to the base.

4. An infusion set as claimed in claim 1 wherein said needle is engaged with the base when moved from the extended position to the retracted position to prevent movement to the extended position from the retracted position.

5. An infusion set as claimed in claim 4 wherein the needle is engaged with the base to prevent movement from the extended position until after a predetermined force has been applied to the needle by the delivery tube.

6. An infusion set as claimed in claim 5 wherein the base is provided with a first detent means which is engagable by the needle when in the extended position to prevent said movement from the extended position.

7. An infusion set as claimed in claim 4 wherein the base is provided with a second detent means which is engaged by the needle when in the retracted position to prevent said movement from the retracted position.

8. An infusion set as claimed in claim 7 wherein at least a portion of the needle accommodated within the base when in the extended position is asymmetric about a central axis of the needle and is received in a passage formed in the base of complementary cross-sectional configuration.

9. An infusion set as claimed in claim 7 wherein a portion of the needle accommodated within the base is supported by a hub member slidably receivable in a passage formed in the base.

10. An infusion set as claimed in claim 9 wherein the hub is engaged with the second detent means.

11. An infusion set as claimed in claim 8 wherein the portion of the needle is convoluted.

12. An infusion set as claimed in claim 1 wherein the engagement means comprises a slider slidably supported from the housing whereby slidable movement of a slider causes said longitudinal movement of the needle.

13. An infusion set as claimed in claim 12 wherein said engagement means comprises a capstan-like element rotatably supported in the housing whereby rotation of a capstan-like element causes said longitudinal movement of the needle.

14. An infusion set as claimed in claim 1 wherein the engagement means in its movement on the housing is not able to effect longitudinal movement of the needle from the retracted position to the extended position.

15. An infusion set as claimed in claim 1 wherein accommodation of the delivery tube within the housing is such as to prevent movement of the delivery tube from the housing into the flexible duct.

16. An infusion set as claimed in claim 2 wherein the needle is not rotatable about a central axis of the needle with respect to the base.

17. An infusion set as claimed in claim 2 wherein said needle is engaged with the base when moved from the extended position to the retracted position to prevent movement to the extended position from the retracted position.

18. An infusion set as claimed in claim 3 wherein said needle is engaged with the base when moved from the extended position to the retracted position to prevent movement to the extended position from the retracted position.

19. An infusion set as claimed in claim 1 wherein the needle is engaged with the base to prevent movement from the extended position until after a predetermined force has been applied to the needle by the delivery tube.

20. An infusion set as claimed in claim 2 wherein the needle is engaged with the base to prevent movement from the extended position until after a predetermined force has been applied to the needle by the delivery tube.

21. An infusion set as claimed in claim 5 wherein the base is provided with a second detent means which is engaged by the needle when in the retracted position to prevent said movement from the retracted position.

22. An infusion set as claimed in claim 6 wherein the base is provided with a second detent means which is engaged by the needle when in the retracted position to prevent said movement from the retracted position.

* * * * *